(12) United States Patent
Åkerfeldt et al.

(10) Patent No.: US 7,329,270 B2
(45) Date of Patent: Feb. 12, 2008

(54) FEMORAL COMPRESSION DEVICE

(75) Inventors: Dan Åkerfeldt, Uppsala (SE); Lars Tenerz, Uppsala (SE); Per Egnelöv, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 567 days.

(21) Appl. No.: 10/322,809

(22) Filed: Dec. 19, 2002

(65) Prior Publication Data

US 2004/0122469 A1 Jun. 24, 2004

(51) Int. Cl.
*A61B 17/00* (2006.01)
(52) U.S. Cl. ...................................... 606/201
(58) Field of Classification Search ................ 606/157, 606/201, 203, 204, 213
See application file for complete search history.

(56) References Cited

U.S. PATENT DOCUMENTS

| | | | | |
|---|---|---|---|---|
| 4,557,262 A | * | 12/1985 | Snow ........................... | 606/201 |
| 5,301,683 A | * | 4/1994 | Durkan ........................ | 600/557 |
| 5,307,811 A | * | 5/1994 | Sigwart et al. .............. | 600/490 |
| 5,514,155 A | * | 5/1996 | Daneshvar ................... | 606/201 |
| 5,542,427 A | | 8/1996 | Akerfeldt | |
| 5,569,297 A | * | 10/1996 | Makower et al. ............ | 606/201 |
| 6,068,646 A | * | 5/2000 | Lam ............................. | 606/203 |
| 6,146,394 A | * | 11/2000 | Morejohn et al. ........... | 606/158 |

FOREIGN PATENT DOCUMENTS

| | | |
|---|---|---|
| EP | 0 462 088 B1 | 11/1995 |
| JP | 5-305093 A | 11/1993 |
| SE | 9002077-7 | 12/1991 |
| SE | 9003271-5 | 12/1991 |
| WO | WO 94/05221 A1 | 3/1994 |
| WO | WO 98/34547 A1 | 8/1998 |

OTHER PUBLICATIONS

U.S. Appl. No. 09/355,736, filed Oct. 21, 1999, Sjogren et al.
U.S. Appl. No. 10/209,974, filed Aug. 2, 2002, Akerfeldt.
U.S. Appl. No. 10/235,859, filed Sep. 6, 2002, Akerfeldt.

* cited by examiner

*Primary Examiner*—Michael J. Hayes
*Assistant Examiner*—Victor Nguyen
(74) *Attorney, Agent, or Firm*—Foley & Lardner LLP

(57) ABSTRACT

The invention provides a femoral compression device (11; 21) for compressing a femoral artery of a patient. The femoral compression device (11; 21) comprises a pressurizing means (12; 22), a compression plate (13; 23) for compressive bearing against a puncture site, a base portion (14; 24) provided with two opposing extensions (15, 16; 25, 26), to the ends of which a belt, which is adapted to be arranged around the patient's body, can be fixed. According to the invention, the pressurizing means is in the form of a spring (12; 22), such as a coil spring (12; 22), the first end of which is connected to the compression plate (13; 23) and the second end of which is operatively connected to a handle (19; 29), which can be operated to adjusting the compression of the spring (12; 22).

33 Claims, 2 Drawing Sheets

FEMORAL COMPRESSION DEVICE

FIELD OF THE INVENTION

The present invention relates generally to a femoral compression device comprising a pressurizing means that presses against a femoral artery of a patient, and more particularly to a femoral compression device comprising a pressurizing means that provides a user with a true indication that the compression pressure being applied on the femoral artery actually is increasing when the pressurizing means is operated to effect such an increase.

BACKGROUND OF THE INVENTION

The present invention is a modification of the femoral compression devices disclosed in the patents U.S. Pat. No. 5,307,811 and EP 0 462 088 B1, which are assigned to the present assignee and which claim priority from SE 9002077 and SE 9003271. A femoral compression device according to these publications comprises basically a pressurizing means for compressive bearing against a puncture site at a femoral artery of a patient, a belt adapted to be fixed around the patient's body, and a base plate supporting the pressurizing means and being provided with two extensions. The pressurizing means according to these publications is a pneumatic device in the form of an inflatable air cushion or balloon, different embodiments of which have also been disclosed in U.S. Pat. No. 5,542,427, WO 94/05221, WO 98/34547 and U.S. application Ser. Nos. 09/355,736, 10/209,974 and 10/235,859, which all are assigned to the present assignee. All of the documents cited in this paragraph are incorporated herein by reference.

In use, the inflatable air cushion is positioned over a femoral artery of a patient, and the belt, which extends from the end of the first extension, around the patient's body and to the end of the second extension, is tightened. Then, the inflatable air cushion is inflated by a hand pump to a certain internal pressure, thereby expanding the air cushion such that the femoral artery is compressed in order to prevent bleeding through a puncture hole being made in the artery wall. The internal pressure, which can be read from a pressure gauge provided on the pump, should be raised to a value between the diastolic pressure and the systolic pressure—which is a procedure that has proven to work very well for the vast majority of patients.

An inherent characteristic of a pneumatic device, and in particular of the inflatable air cushion described above, is that the internal pressure only within a certain operating range corresponds to an increased length of stroke (i.e. increased expansion of the air cushion). For a pressurizing means in the form of an inflatable air cushion, this feature implies that when the air cushion has reached its maximal expansion, a further increase of the internal pressure does not expand the air cushion any more, which, in turn, means that no more compression pressure can be applied on the femoral artery. Normally, i.e. for the vast majority of patients having a normal or ordinary body constitution, this is of no problem since the length of stroke (i.e. the expansion) of the air cushion corresponds to the expansion needed to completely, or almost completely, compress the artery such that the flow of blood therethrough is significantly reduced, to thereby prevent bleeding from the puncture wound. In other words, the operating range of the air cushion ranges from a minimum value where the flow of blood is essentially unrestricted to a maximum value where the flow of blood is essentially completely stopped.

However, for those patients where the femoral artery is embedded in a very thick layer of adipose tissue, it can be difficult to determine whether the air cushion has reached its maximal expanded state, in which no more compression of the femoral artery is possible. And when a pressure gauge is used, this problem is even more pronounced because the pressure gauge continues to show increasing values even though the air cushion has reached its maximal expansion. This behaviour may give an inexperienced user a deceitful impression that the compression pressure on the femoral artery actually is increasing. Needless to say, such a misjudgement may give rise to very serious complications.

Another disadvantage with an inflatable air cushion is that if the patient moves, e.g. bends forward, after the femoral compression device has been positioned around the patient's body, the compression pressure on the femoral artery is drastically reduced, because an air cushion, which only contains a small volume of air, has essentially no internal resilience. In other words, if there is a difference in the distance between the base plate and the femoral artery for the two different postures of the patient, the air cushion cannot compensate for this difference, which implies that there is essentially no compression pressure applied for the posture involving the longer distance between the base plate and the femoral artery.

SUMMARY OF THE INVENTION

One object of the present invention is therefore to provide a femoral compression device comprising a pressurizing means that indicates whether more compression pressure actually is being applied on the femoral artery when a user operates the pressurizing means in order to effectuate such an increase in compression pressure.

Another object of the present invention is to provide a femoral compression device comprising a pressurizing means that has a comparatively large internal resilience, so that the compression device is comparatively insensitive to movements of the patient.

These objects are achieved with a femoral compression device comprising a pressurizing means in the form of a compression plate provided with a spring. Such a spring-loaded compression plate has the advantage that the force (and thereby the compression pressure) being applied on the puncture site is directly proportional to the energy loaded into the spring, i.e. proportional to how much the spring is compressed. When the spring, which is operated by a handle or the like, is completely compressed, a user is provided with an indication that the maximal compression has been reached and that no more compression pressure can be applied on the puncture site in question. Preferably, the femoral compression device according to the present invention is also provided with a gauge that displays the compression pressure being applied on the puncture site in question.

An advantage with such a spring-loaded pressurizing means is that a spring has some internal resilience, which can compensate for some difference in the distance between the base plate and the femoral artery, thereby being comparatively less sensitive to movements of the patient.

DESCRIPTION OF THE PREFERRED EMBODIMENTS

Figure 1:
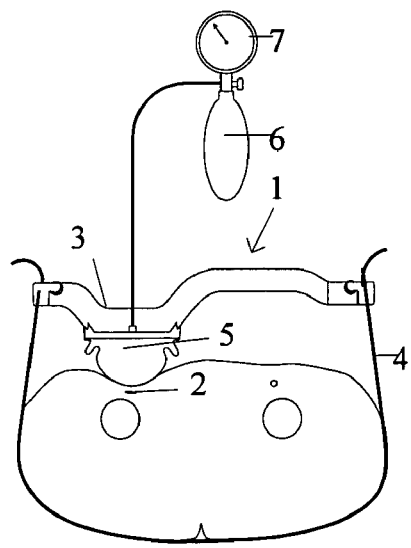
FIG. 1 is a cross-sectional view of a previously proposed femoral compression device attached to the body of a patient having a normal amount of adipose tissue overlying a femoral artery.

FIG. 1 illustrates how a previously proposed femoral compression device 1 is attached to the body of a patient in order to apply compression pressure on a femoral artery 2 in which a puncture hole has been made. The compression device 1 comprises basically a base plate 3, a belt 4 and an inflatable air cushion 5, which can be inflated by a pump 6, which is provided with a pressure gauge 7.

The patient illustrated in FIG. 1 has a normal body constitution, with an average amount of adipose tissue being localised between the skin and the femoral artery 2. When in a semi-inflated state, i.e. less than fully expanded, the air cushion 5 can therefore compress the artery 2 such that no blood penetrates through the puncture hole in the femoral artery 2. Herein, the expression "normal body constitution" refers to a body constitution to which this existing femoral compression device 1 is adapted, i.e. the length of stroke (the expansion) of the air cushion 5 is sufficient for the pressure force being applied therewith to be transmitted through the layer of adipose tissue and compress the femoral artery 2.

Figure 2:
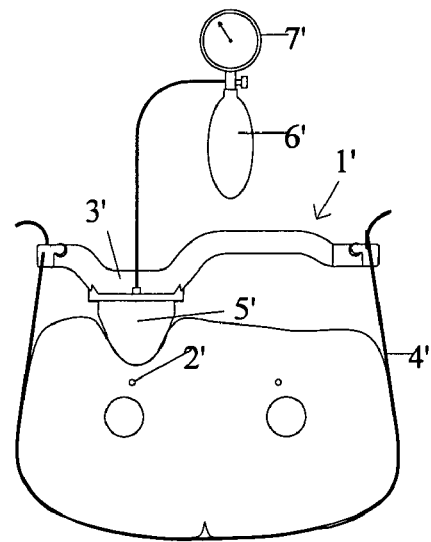
FIG. 2 is a cross-sectional view of a previously proposed femoral compression device attached to the body of a patient having an excessive amount of adipose tissue overlying a femoral artery.

Another case is illustrated in FIG. 2, where a femoral compression device 1' has been attached to the body of an overweight patient to apply compression pressure on a femoral artery 2' in which a puncture hole has been made. The femoral compression device 1' of FIG. 2 is identical with the femoral compression device 1 shown in FIG. 1, and comprises basically a base plate 3', a belt 4' and an inflatable air cushion 5', which can be inflated by a pump 6', which is provided with a pressure gauge 7'. In this case, an excessive amount of adipose tissue is localised between the skin and the femoral artery 2'. This previously proposed femoral compression device 1' was not designed for this type of patient, and, as is illustrated in the figure, even in the fully expanded state, the air cushion 5' cannot compress the femoral artery 2' enough to stop bleeding through the puncture hole therein. In particular it should be noted that pressure gauges 7 and 7' display the same internal pressure for the two cases illustrated in FIG. 1 and FIG. 2, respectively.

As discussed above, a further inflation of the air cushion 5' of FIG. 2 results only in an increase in the internal pressure within the air cushion 5', without any more compression pressure being applied on the femoral artery 2'. Furthermore, the read-out from the pressure gauge 7' will—at least in some sense—support and justify such an operation by the user, because the pressure gauge 7' will continue to show increasing values and thereby give the user the impression that more compression pressure actually is being applied on the femoral artery 2'. In short: when in a not fully expanded state (as in FIG. 1), more compression pressure is actually applied on the femoral artery 2 when the air cushion 5 is inflated by the pump 6, which is in accordance with the readings from the pressure gauge 7; whereas in a fully expanded state (as in FIG. 2), no more compression pressure is applied on the femoral artery 2' when the air cushion 5' is inflated by the pump 6', which is in contradiction to the readings from the pressure gauge 7'.

In the situation illustrated in FIG. 2, an inexperienced user may continue to operate the pump 6' in an (vain) attempt to apply more compression pressure on the femoral artery 2', and when the user realizes that the bleeding is not going to stop, there is a risk that the decision will be that the compression device 1' has been misplaced and has to be moved to another position, which leads to unnecessary bleeding. Here it should be mentioned that extra tightening of the belt 4' to a large extent could compensate for the above-mentioned disadvantage of the known femoral compression device 1'. However, this procedure requires careful consideration by the user, and the risk of a misleading reading from the pressure gauge 7' is still present.

Figure 3:
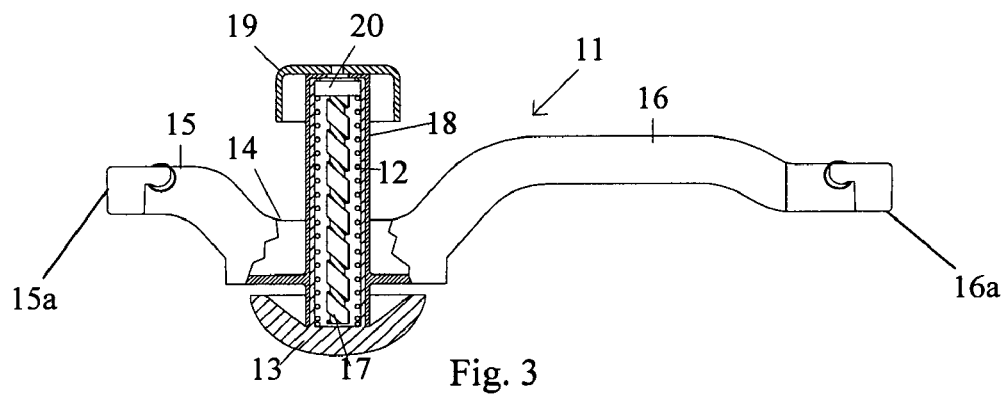
FIG. 3 illustrates a first embodiment of a femoral compression device according to the present invention, wherein a pressurizing means is shown in an essentially unexpanded state.

In FIG. 3 is illustrated a first embodiment of a femoral compression device 11 according to the present invention. The compression device 11 comprises a pressurizing means 12, which is connected to a compression plate 13 being adapted for bearing against a puncture site, and a base portion 14, which is provided with two opposing extensions 15 and 16, to which a belt (not shown in figure) can be attached via devices 15a and 16a. In this first embodiment of a compression device 11 according to the present invention, the pressurizing means 12 is in the form of a coil spring 12, which, together with an adjusting screw 17, is provided in a housing 18, which is arranged generally perpendicular to the base portion 14. A handle 19 is provided at the upper end of the housing 18 and is connected to the upper end of the adjusting screw 17. The adjusting screw 17 is threaded through a threaded washer 20, which bears against the upper end of the coil spring 12. The compression device 11 is in FIG. 3 shown in an initial or relaxed state, in which the coil spring 12 has its maximal extension, i.e. the coil spring 12 is essentially uncompressed.

Figure 4:
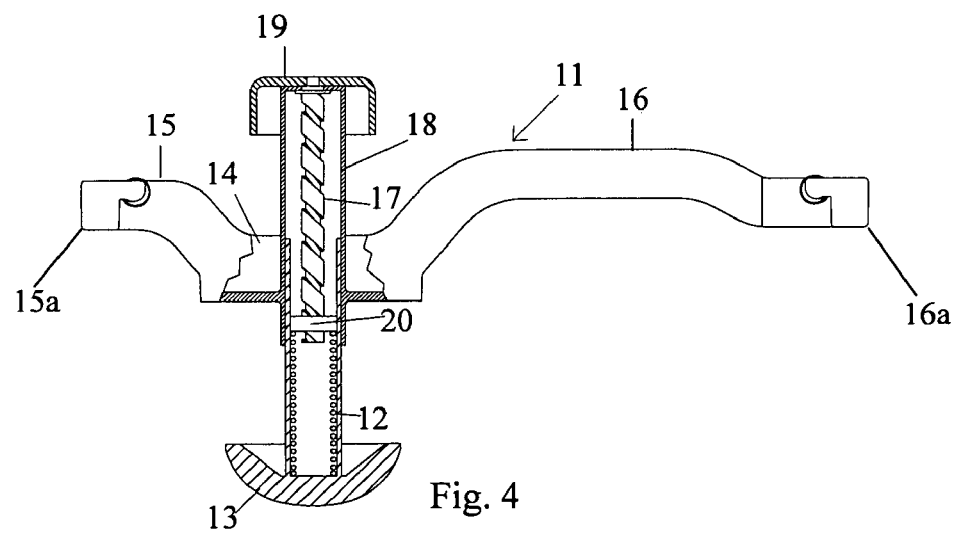
FIG. 4 illustrates the femoral compression device of FIG. 3, wherein the pressurizing means is shown in an expanded state.

When the handle 19 is turned, the threaded washer 20 moves downwards along the adjusting screw 17, thereby compressing the coil spring 12, as is illustrated in FIG. 4. When the femoral compression device 11 is attached to the body of a patient, the compression pressure being applied on the femoral artery can thereby be adjusted by turning the handle 19. According to Hook's law, the force with which the compression plate 13 presses against the puncture site is proportional to the compression of the coil spring 12. This implies that the more the coil spring 12 is compressed, the more compression pressure is applied on the femoral artery in question. In other words, when the pressurizing means is in the form of a coil spring, there is no state of operation in which more energy can be loaded into the pressurizing means without more compression pressure being applied on the femoral artery.

Figure 5:
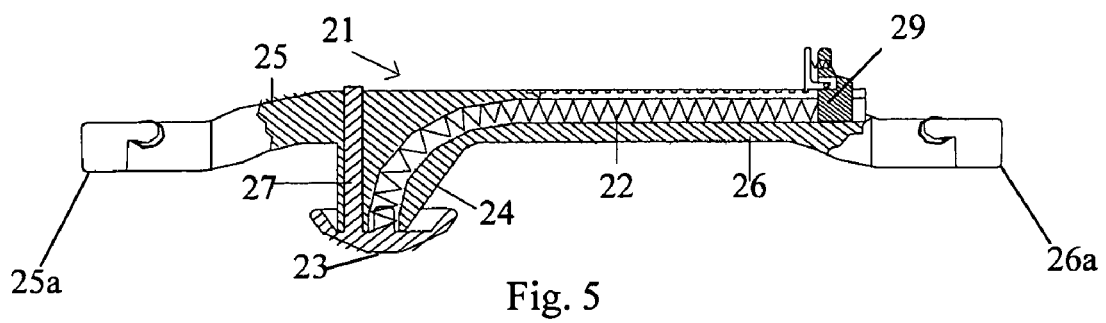
FIG. 5 illustrates a second embodiment of a femoral compression device according to the present invention, wherein pressurizing means is shown in an essentially unexpanded state.

A second embodiment of a compression device 21 according to the present invention is illustrated in FIG. 5. The compression device 21 comprises a pressurizing means 22, which is connected to a compression plate 23 being adapted for bearing against a puncture site, and a base portion 24, which is provided with two opposing extensions 25 and 26, to which a belt (not shown in the figure) can be attached via devices 25a and 26a. The pressurizing means 22 is in the form of a coil spring 22, which partly is arranged in one of the two extensions 26 and partly in the base portion 24. Apparently, this arrangement of the coil spring 22 makes efficient use of the available space within the extension 26 and base portion 24. A handle 29 is provided at the extension 26 in which the spring coil 22 is arranged, and is connected to the first end of the coil spring 22, the second end of which is connected to the compression plate 23. The handle 29, which is variable along the extension 26, is provided with a locking mechanism, so that the handle 29 can be moved, against the action of the coil spring 22, and be locked in any position along the extension 26. The compression plate 23 is further provided with a guide rod 27, which is slidable within a guide hole provided inside the base portion 24. The purpose of the guide rod 27 and the corresponding guide hole is to provide a stable and reliable movement of the compression plate 23. The guide rod 27 and the guide hole can preferably have non-cylindrical cross-sections, which prevents the guide rod 27 from rotating inside the guide hole. The compression device 21 is in FIG. 5 shown in an initial or relaxed state, in which the coil spring 22 has its maximal extension, i.e. the coil spring 22 is essentially uncompressed.

Figure 6:
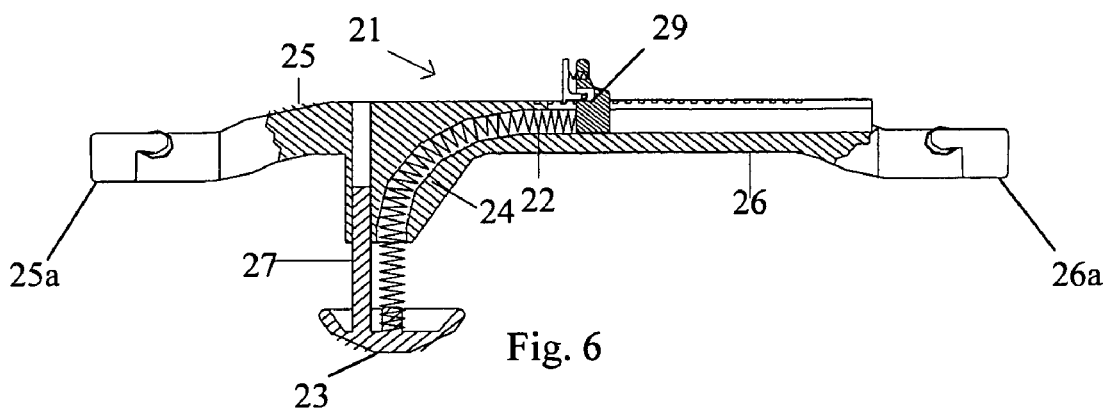
FIG. 6 illustrates the femoral compression device of FIG. 5, wherein the pressurizing means is shown in an expanded state.
Figure 7:
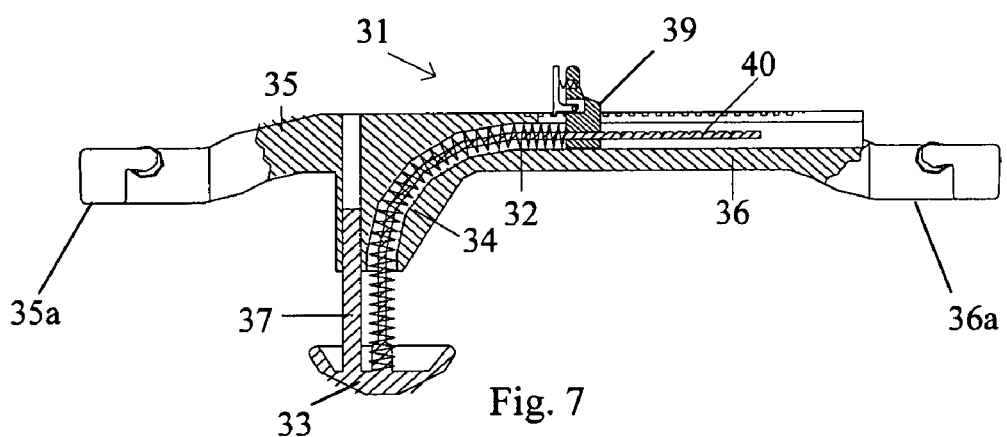
FIG. 7 illustrates how the second embodiment of a femoral compression device can be provided with a measuring rod for indicating the applied compression pressure.

A femoral compression device according to the invention is preferably provided with some kind of gauge that indicates the amount of compression being applied on the puncture site in question. For a compression device having the pressurizing means in the form of a spring, the applied compression pressure is directly related the compression of the spring, and FIG. 7 illustrates how such a gauge could be provided for the second embodiment that was described in conjunction with FIG. 5 and FIG. 6. The femoral compression device 31 shown in FIG. 7 is identical with the femoral compression device 21 of FIG. 5 and FIG. 6, except that the femoral compression device 31 further comprises a flexible measuring rod (or gauge) 40, which extends from a compression plate 33 and into an extension 36 in which a coil spring 32 is provided. By observing the position of a point on the measuring rod 40 in relation to a handle 39, a user is provided with an indication of how much the spring coil 32 is compressed. A scale could be provided along the length of the measuring rod 40, so that a user can observe how much the measuring rod 40 extends behind (in FIG. 7, to the right of) the handle 39. The scale could be graded in Newton (N), i.e. showing the compression force from the coil spring 32, or—perhaps more preferably—the scale could indicate the compression pressure and be graded in, for example, mmHg. The compression pressure is the force from the coil spring 32 divided by the effective area of the compression plate 33. A similar measuring arrangement could be made for the first embodiment of a femoral compression device 11 described in conjunction with FIG. 3 and FIG. 4. In that case, the compression plate 13 could be provided with a measuring rod that extends through the washer 20, such that the compression of the spring coil 12 can read by observing how much the measuring rod extends through the washer 20. As with the other embodiments, device 31 is secured to a patient via a belt (not shown in the figure) and devices 35a and 36a.

Although the present invention has been described with reference to specific embodiments, also shown in the appended drawings, it will be apparent for those skilled in the art that many variations and modifications can be done within the scope of the invention as described in the specification and defined with reference to the following claims. Especially, it should be noted that other types of springs (such as a leaf spring or laminated type of spring) and elastic members could be used, which springs and elastic members, accordingly, could be arranged in various ways, and that other types of arrangements for providing a user with an indication of the applied compression pressure could be provided. The springs could be made from plastics or metals, including alloys, such as Nitinol. Also, the invention can be applied to compress arteries other than the femoral artery.

What is claimed is:

1. A femoral compression device for compressing a femoral artery of a patient, comprising a spring, a compression plate for compressive bearing against a puncture site, and a base portion provided with two opposing extensions, each of the two opposing extensions comprising a device for affixing a belt, which is adapted to be arranged around the patient's body,
    wherein a first end of the spring is connected to the compression plate and a second end of the spring is operatively connected to a handle, which is operable to adjust the compression of the spring independently of force exerted on the compression plate.

2. A femoral compression device according to claim 1, wherein the femoral compression device is provided with a gauge that indicates the amount of compression pressure being applied against the puncture site.

3. A femoral compression device according to claim 2, wherein the gauge indicates the compression of the spring.

4. A femoral compression device according to claim 2, wherein the gauge indicates the amount of compression pressure being applied against the puncture site in mmHg.

5. A femoral compression device according to claim 1, wherein the first end of the spring is connected to the compression plate and the spring, together with an adjusting screw, is provided in a housing, the upper end of the adjusting screw being connected to a handle and the adjusting screw being threaded through a washer, which bears against the second end of the spring, so that, by turning the handle, the washer moves along the adjusting screw to thereby adjust the compression of the spring.

6. A femoral compression device according to claim 5, wherein the compression plate is provided with a measuring rod that extends through the washer, which measuring rod indicates the distance from the compression plate to the washer and thereby the compression of the spring.

7. A femoral compression device according to claim 1, wherein the first end of the spring is connected to the compression plate, the spring extends through the base portion and at least partly into one of the extensions, and the second end of the spring is connected to a handle, which is slidable along said extension and which is lockable at a desired position, so that the compression of the spring can be adjusted by moving the handle.

8. A femoral compression device according to claim 7, wherein the compression plate is provided with a guide rod that extends into a corresponding guide hole provided in the base portion.

9. A femoral compression device according to claim 7, wherein the compression plate is provided with a measuring rod that extends into the extension in which the spring is arranged, which measuring rod indicates the distance from the compression plate to the handle and thereby the compression of the spring.

10. A femoral compression device according to claim 1, wherein the femoral compression device is provided with a gauge that indicates the amount of compression pressure being applied against the puncture site.

11. A femoral compression device according to claim 1, wherein the spring comprises a coil spring.

12. A femoral compression device according to claim 1, wherein the spring comprises a leaf spring.

13. A femoral compression device according to claim 1, wherein the spring comprises a laminated spring.

14. A femoral compression device according to claim 1, wherein the spring is made from plastic.

15. A femoral compress ion device according to claim 1, wherein the spring is made from metal.

16. A femoral compression device according to claim 1, wherein the spring is made from Nitinol.

17. A femoral compression device according to claim 1, wherein the spring is made from an alloy.

18. A femoral compression device for compressing a femoral artery of a patient, comprising a spring, a compression plate for compressive bearing against a puncture site, and a base portion provided with two opposing extensions, each of the two opposing extensions comprising a device for affixing a belt, which is adapted to be arranged around the patient's body, wherein a first end of the spring is connected to the compression plate and a second end of the spring is operatively connected to a handle such that when the handle is moved a position of the second end of the spring moves relative to the base portion.

19. A femoral compression device according to claim 18, wherein the femoral compression device is provided with a gauge that indicates the amount of compression pressure being applied against the puncture site.

20. A femoral compression device according to claim 19, wherein the gauge indicates the compression of the spring.

21. A femoral compression device according to claim 19, wherein the gauge indicates the amount of compression pressure being applied against the puncture site in mmHg.

22. A femoral compression device according to claim 18, wherein the spring, together with an adjusting screw, is provided in a housing, the upper end of the adjusting screw being connected to the handle and the adjusting screw being threaded through a washer, which bears against the second end of the spring, so that, by turning the handle, the washer moves along the adjusting screw to thereby adjust the compression of the spring.

23. A femoral compression device according to claim 22, wherein the compression plate is provided with a measuring rod that extends through the washer, which measuring rod indicates the distance from the compression plate to the washer and thereby the compression of the spring.

24. A femoral compression device according to claim 18, wherein the spring extends through the base portion and at least partly into one of the extensions, and the handle is lockable at a desired position.

25. A femoral compression device according to claim 24, wherein the compression plate is provided with a guide rod that extends into a corresponding guide hole provided in the base portion.

26. A femoral compression device according to claim 24, wherein the compression plate is provided with a measuring rod that extends into the extension in which the spring is arranged, which measuring rod indicates the distance from the compression plate to the handle and thereby the compression of the spring.

27. A femoral compression device according to claim 18, wherein the spring comprises a coil spring.

28. A femoral compression device according to claim 18, wherein the spring comprises a leaf spring.

29. A femoral compression device according to claim 18, wherein the spring comprises a laminated spring.

30. A femoral compression device for compressing a femoral artery of a patient, comprising a spring, a compression plate for compressive bearing against a puncture site, and a base portion provided with two opposing extensions, each of the two opposing extensions comprising a device for affixing a belt, which is adapted to be arranged around the patient's body, wherein one end of the spring is connected to the compression plate and another end of the spring is operatively connected to a handle such that when the handle is moved a position of an end of the spring moves relative to the base portion independently of force exerted on the compression plate.

31. A femoral compression device according to claim 30, wherein the femoral compression device is provided with a gauge that indicates the amount of compression pressure being applied against the puncture site.

32. A femoral compression device according to claim 30, wherein the handle is configured to move by rotating around an axis.

33. A femoral compression device according to claim 30, wherein the handle is configured to move along one of the two opposing extensions.

* * * * *